(12) United States Patent
Leven (10) Patent No.: US 9,744,345 B2
(45) Date of Patent: Aug. 29, 2017

(54) LEADS WITH PROXIMAL STIFFENING AND RELATED METHODS OF USE AND MANUFACTURE

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/852,070

(22) Filed: Sep. 11, 2015

(65) Prior Publication Data

US 2016/0001061 A1 Jan. 7, 2016

Related U.S. Application Data

(62) Division of application No. 14/103,245, filed on Dec. 11, 2013, now abandoned.
(Continued)

(51) Int. Cl.
*A61N 1/05* (2006.01)
*B29C 41/20* (2006.01)
(Continued)

(52) U.S. Cl.
CPC ............ *A61N 1/05* (2013.01); *A61N 1/0551* (2013.01); *B29C 41/20* (2013.01); *B29K 2063/00* (2013.01); *B29L 2031/753* (2013.01)

(58) Field of Classification Search
CPC .......... A61N 1/04; A61N 1/05; A61N 1/0551; B29C 41/20
(Continued)

(56) References Cited

U.S. PATENT DOCUMENTS 3,077,639 A * 2/1963 Siner ...................... H01C 17/02
156/155
3,270,227 A * 8/1966 Kaeding .............. H02K 5/1672
310/90
(Continued)

OTHER PUBLICATIONS

Official Communication for U.S. Appl. No. 14/103,245 dated Apr. 8, 2015.
(Continued)

*Primary Examiner* — Christopher A Flory
(74) *Attorney, Agent, or Firm* — Lowe Graham Jones PLLC; Bruce E. Black (57) ABSTRACT

An electrical stimulation lead includes a lead body; electrodes disposed along the distal portion of the lead body or on a paddle body coupled to the lead body; terminals disposed along the proximal portion of the lead body; and conductors coupling the terminals to the electrodes. The lead also includes a conductor guide disposed within the lead body and extending from the proximal portion of the lead body. The conductor guide defines a central lumen and a plurality of conductor lumens disposed around the central lumen. The lead further includes a stiffening agent disposed within at least one of the conductor lumens. The stiffening agent includes a) a material formed from a granular particulate material, b) a polymeric material having a durometer at least 10% greater than the durometer of the conductor guide, or c) a continuous epoxy layer within which discrete epoxy particles are also disposed.

20 Claims, 10 Drawing Sheets

Related U.S. Application Data (60) Provisional application No. 61/745,407, filed on Dec. 21, 2012.

(51) Int. Cl.
    *B29K 63/00* (2006.01)
    *B29L 31/00* (2006.01)

(58) Field of Classification Search
    USPC .................................. 607/2, 116; 600/373
    See application file for complete search history.

(56) References Cited

U.S. PATENT DOCUMENTS

| | | | |
|---|---|---|---|
| 3,592,702 A * | 7/1971 | Dehn | C21D 9/32 148/206 |
| 3,832,192 A * | 8/1974 | McIntosh | C04B 35/48 361/321.5 |
| 5,069,664 A * | 12/1991 | Guess | A61B 17/2202 600/442 |
| 5,429,597 A * | 7/1995 | DeMello | A61M 25/005 604/103.09 |
| 5,796,044 A * | 8/1998 | Cobian | A61N 1/056 174/103 |
| 5,906,606 A * | 5/1999 | Chee | A61M 25/005 604/246 |
| 6,181,969 B1 | 1/2001 | Gord | |
| 6,249,708 B1 | 6/2001 | Nelson et al. | |
| 6,315,757 B1 | 11/2001 | Chee et al. | |
| 6,516,227 B1 | 2/2003 | Meadows et al. | |
| 6,607,502 B1 * | 8/2003 | Maguire | A61B 17/2202 604/22 |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,916,393 B2 * | 7/2005 | Ohzuru | B32B 27/34 156/137 |
| 6,978,185 B2 * | 12/2005 | Osypka | A61N 1/056 607/122 |
| 7,037,290 B2 | 5/2006 | Gardeski et al. | |
| 7,051,419 B2 * | 5/2006 | Schrom | A61N 1/0551 29/592.1 |
| 7,065,411 B2 | 6/2006 | Verness | |
| 7,158,837 B2 * | 1/2007 | Osypka | A61N 1/056 439/909 |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,019,439 B2 | 9/2011 | Kuzma et al. | |
| 8,175,710 B2 | 5/2012 | He | |
| 8,224,450 B2 | 7/2012 | Brase | |
| 8,364,278 B2 | 1/2013 | Pianca et al. | |
| 8,406,883 B1 * | 3/2013 | Barker | H01R 24/58 607/116 |
| 8,425,549 B2 * | 4/2013 | Lenker | A61B 17/12118 606/198 |
| 8,886,336 B2 * | 11/2014 | Lim | A61N 1/05 607/116 |
| 9,486,143 B2 * | 11/2016 | Hoseit | A61B 5/0095 |
| 2001/0039301 A1 * | 11/2001 | Ishikawa | C09D 11/02 523/161 |
| 2002/0117330 A1 * | 8/2002 | Eldridge | B23K 20/004 174/260 |
| 2002/0165461 A1 * | 11/2002 | Hayzelden | A61B 18/1492 600/523 |
| 2002/0165534 A1 * | 11/2002 | Hayzelden | A61M 25/0144 606/41 |
| 2003/0208198 A1 * | 11/2003 | Hayzelden | A61B 18/1492 606/41 |
| 2004/0014355 A1 * | 1/2004 | Osypka | A61N 1/056 439/502 |
| 2004/0210289 A1 * | 10/2004 | Wang | A61K 9/5094 607/116 |
| 2005/0175062 A1 * | 8/2005 | Bowman | H05B 7/14 373/95 |
| 2005/0283135 A1 * | 12/2005 | Pepin | A61L 29/085 604/525 |
| 2006/0002446 A1 * | 1/2006 | Bowman | H05B 7/14 373/92 |
| 2006/0142703 A1 | 6/2006 | Carter et al. | |
| 2007/0150036 A1 | 6/2007 | Anderson | |
| 2007/0168004 A1 * | 7/2007 | Walter | A61N 1/0551 607/116 |
| 2007/0168007 A1 | 7/2007 | Kuzma et al. | |
| 2007/0228110 A1 * | 10/2007 | Eldridge | B23K 20/004 228/180.5 |
| 2008/0208166 A1 * | 8/2008 | Goode | A61M 25/0662 604/510 |
| 2009/0054949 A1 * | 2/2009 | Alexander | A61N 1/05 607/37 |
| 2009/0222073 A1 * | 9/2009 | Flowers | A61N 1/3752 607/116 |
| 2011/0152989 A1 * | 6/2011 | Tan | A61N 1/056 607/122 |
| 2011/0319948 A1 * | 12/2011 | Onodera | A61B 5/0422 607/5 |
| 2013/0267853 A1 * | 10/2013 | Dausch | B06B 1/0607 600/466 |
| 2014/0058488 A1 * | 2/2014 | Leven | A61N 1/05 607/116 |
| 2014/0155969 A1 * | 6/2014 | Leven | A61N 1/0551 607/116 |
| 2014/0163664 A1 * | 6/2014 | Goldsmith | A61B 17/00491 623/1.11 |
| 2014/0180128 A1 * | 6/2014 | Corl | A61B 8/445 600/467 |
| 2016/0317804 A1 * | 11/2016 | Flowers | A61N 1/3752 |

OTHER PUBLICATIONS

Official Communication for U.S. Appl. No. 14/103,245 dated Jun. 22, 2015.

\* cited by examiner

Fig. 8

LEADS WITH PROXIMAL STIFFENING AND RELATED METHODS OF USE AND MANUFACTURE

CROSS-REFERENCE TO RELATED APPLICATIONS

This application is a divisional of U.S. patent application Ser. No. 14/103,245 filed Dec. 11, 2013 which claims the benefit under 35 U.S.C. §119(e) of U.S. Provisional Patent Application Ser. No. 61/745,407 filed Dec. 21, 2012, both of which are incorporated herein by reference.

FIELD

The present invention is directed to the area of implantable electrical stimulation systems and methods of making and using the systems. The present invention is also directed to implantable electrical stimulation leads having proximal stiffening, as well as methods of making and using the leads and electrical stimulation systems.

BACKGROUND

Implantable electrical stimulation systems have proven therapeutic in a variety of diseases and disorders. For example, spinal cord stimulation systems have been used as therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. It may thus be seen that electrical stimulation systems or stimulators have been developed to provide therapy for a variety of treatments.

A stimulator may include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to the body tissue. The proximal end of the leads is connected to the pulse generator while the distal end of the leads is connected to the stimulator electrodes. Since the leads are thin and perhaps weak, the proximal arrays or areas of the leads may be subject to buckling and other mechanical failures due to the rigors of clinical use.

BRIEF SUMMARY

One embodiment is an electrical stimulation lead including a lead body having a distal portion, a proximal portion, and a longitudinal length; a plurality of electrodes disposed along the distal portion of the lead body or on a paddle body coupled to the lead body; a plurality of terminals disposed along the proximal portion of the lead body; and a plurality of conductors coupling the plurality of terminals to the plurality of electrodes. The lead also includes a conductor guide disposed within the lead body and extending from the proximal portion of the lead body along the lead body. The conductor guide defines a central lumen and a plurality of conductor lumens disposed around the central lumen. The central lumen and conductor lumens extend longitudinally along the conductor guide. The conductor lumens have a proximal end and receive the plurality of conductors within the conductor lumens. The lead further includes a stiffening agent disposed within at least one of the conductor lumens from the proximal end to at least a portion of the conductor lumen within which at least one of the conductors is disposed. The stiffening agent includes a material formed from a granular particulate material disposed within the conductor lumen.

Another embodiment is an electrical stimulation lead including a lead body having a distal portion, a proximal portion, and a longitudinal length; a plurality of electrodes disposed along the distal portion of the lead body or on a paddle body coupled to the lead body; a plurality of terminals disposed along the proximal portion of the lead body; and a plurality of conductors coupling the plurality of terminals to the plurality of electrodes. The lead also includes a conductor guide disposed within the lead body and extending from the proximal portion of the lead body along the lead body. The conductor guide includes a polymeric material and defines a central lumen and a plurality of conductor lumens disposed around the central lumen. The central lumen and conductor lumens extend longitudinally along the conductor guide. The conductor lumens have a proximal end and receive the plurality of conductors within the conductor lumens. The lead further includes a stiffening agent disposed within at least one of the conductor lumens from the proximal end to at least a portion of the conductor lumen within which at least one of the conductors is disposed. The stiffening agent is a polymeric material has a durometer at least 10% greater than a durometer of the polymeric material of the conductor guide.

Yet another embodiment is an electrical stimulation lead including a lead body having a distal portion, a proximal portion, and a longitudinal length; a plurality of electrodes disposed along the distal portion of the lead body or on a paddle body coupled to the lead body; a plurality of terminals disposed along the proximal portion of the lead body; and a plurality of conductors coupling the plurality of terminals to the plurality of electrodes. The lead also includes a conductor guide disposed within the lead body and extending from the proximal portion of the lead body along the lead body. The conductor guide defines a central lumen and a plurality of conductor lumens disposed around the central lumen. The central lumen and conductor lumens extend longitudinally along the conductor guide. The conductor lumens have a proximal end and receive the plurality of conductors within the conductor lumens. The lead further includes a stiffening agent disposed within at least one of the conductor lumens from the proximal end to at least a portion of the conductor lumen within which at least one of the conductors is disposed. The stiffening agent includes discrete epoxy particles and a continuous epoxy layer within which the epoxy particles are disposed.

A further embodiment is a method of making an electrical stimulation lead that includes disposing a plurality of conductor wires into a plurality of conductor lumens defined within a conductor guide. The conductor lumens extend longitudinally from a proximal end of the conductor guide. At least one of the conductor lumens defines an open portion that extends distally from the proximal end of the conductor guide and does not contain any portion of the conductor wires. The method further includes disposing a plurality of terminals along the proximal portion of the conductor guide in a spaced-apart longitudinal arrangement; electrically coupling each of the plurality of terminals to at least one of the conductors; flowing epoxy material into the open portion of at least one of the conductor lumens; curing the epoxy material; breaking the cured epoxy material into discrete epoxy particles; flowing additional epoxy material into the open portion of at least one of the conductor lumens and around the epoxy particles; and curing the additional epoxy material to form a continuous epoxy layer having the epoxy particles disposed therein.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having proximal stiffening, as well as methods of making and using the leads and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads. and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
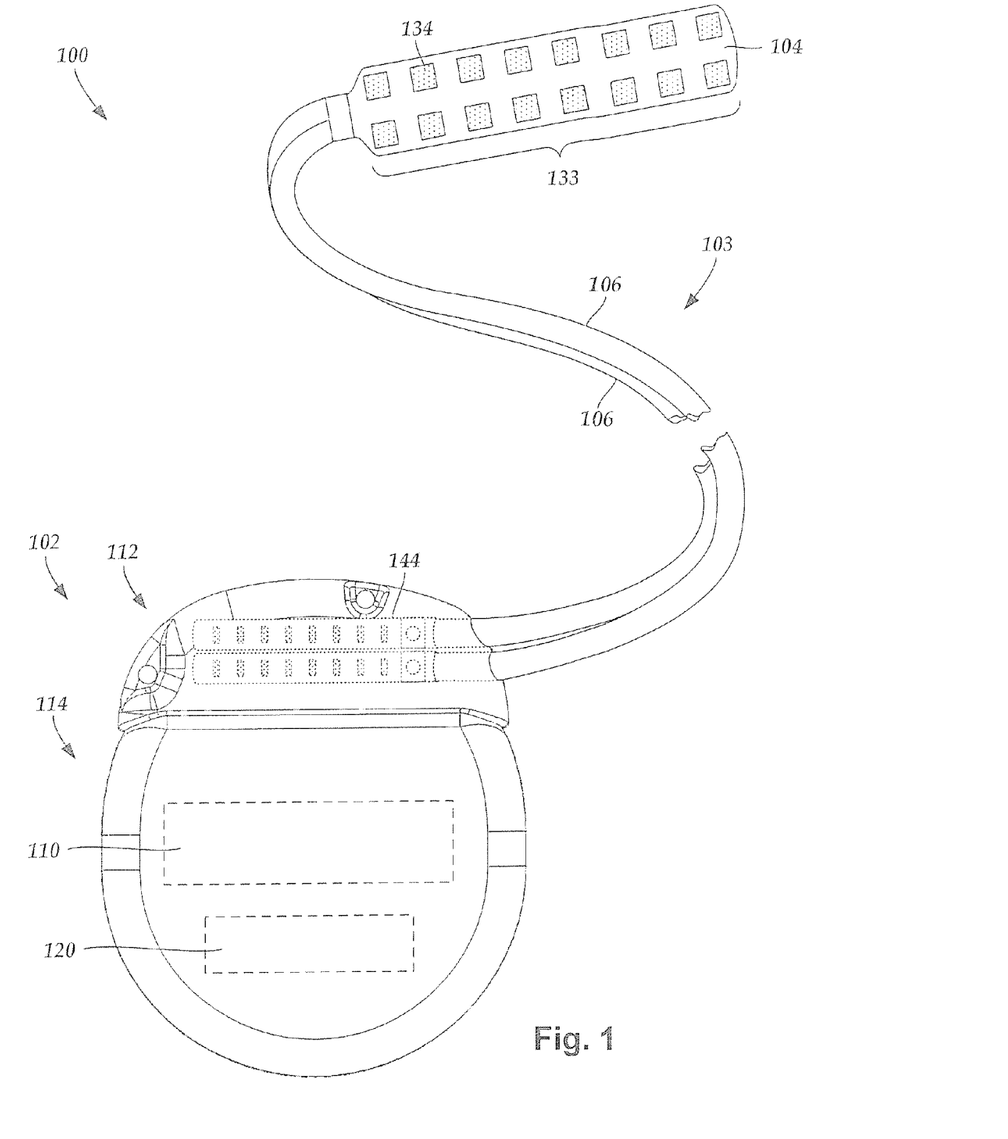
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system 100 includes a control module (e.g., a stimulator or pulse generator) 102 and a lead 103 coupleable to the control module 102. The lead 103 includes a paddle body 104 and one or more lead bodies 106 that have a distal portion, a proximal portion, and a longitudinal length. The longitudinal length extends from the distal portion of the lead body to the proximal portion of the lead body. In this figure, the lead 103 includes a paddle body 104 coupled at the distal end of the lead 103 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIGS. 3A-3B) is disposed at the proximal end of each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
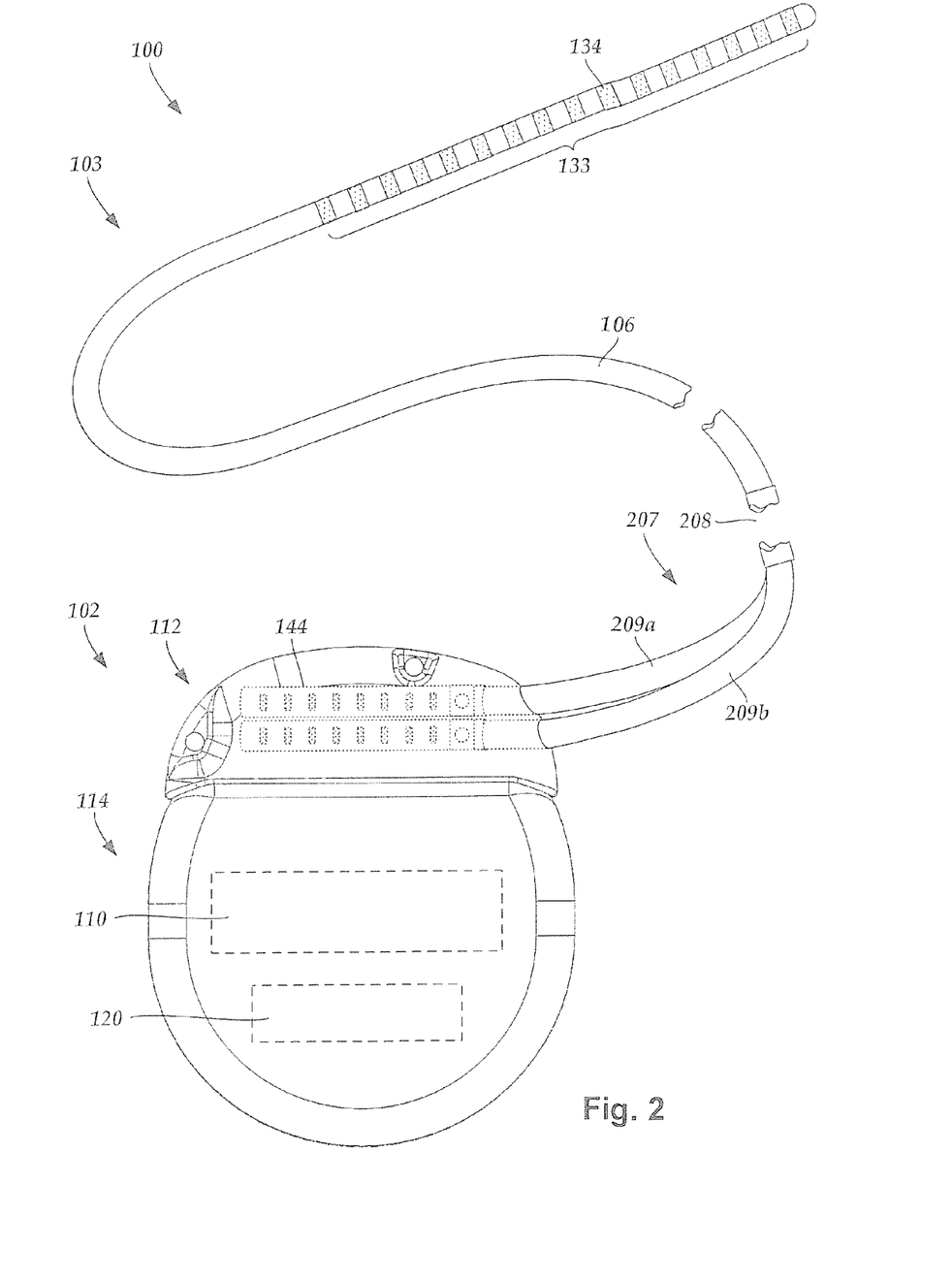
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the distal end of the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupled directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
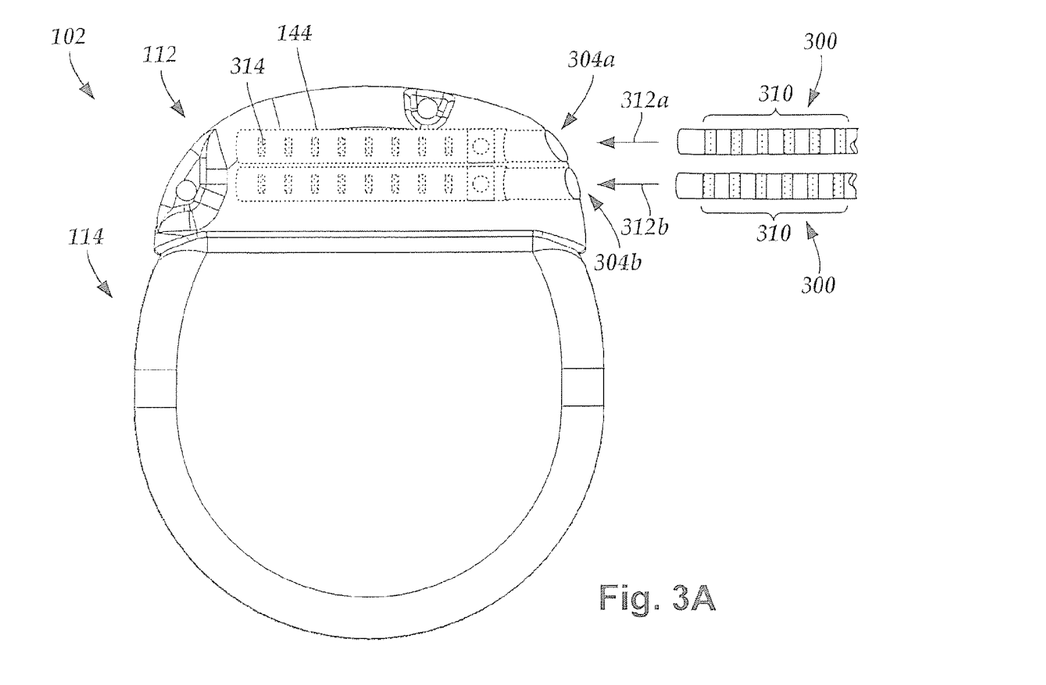
FIG. 3A is a schematic view of one embodiment of the control module of FIG. 1 configured and arranged to electrically couple to an elongated device, according to the invention.
Figure 3B:
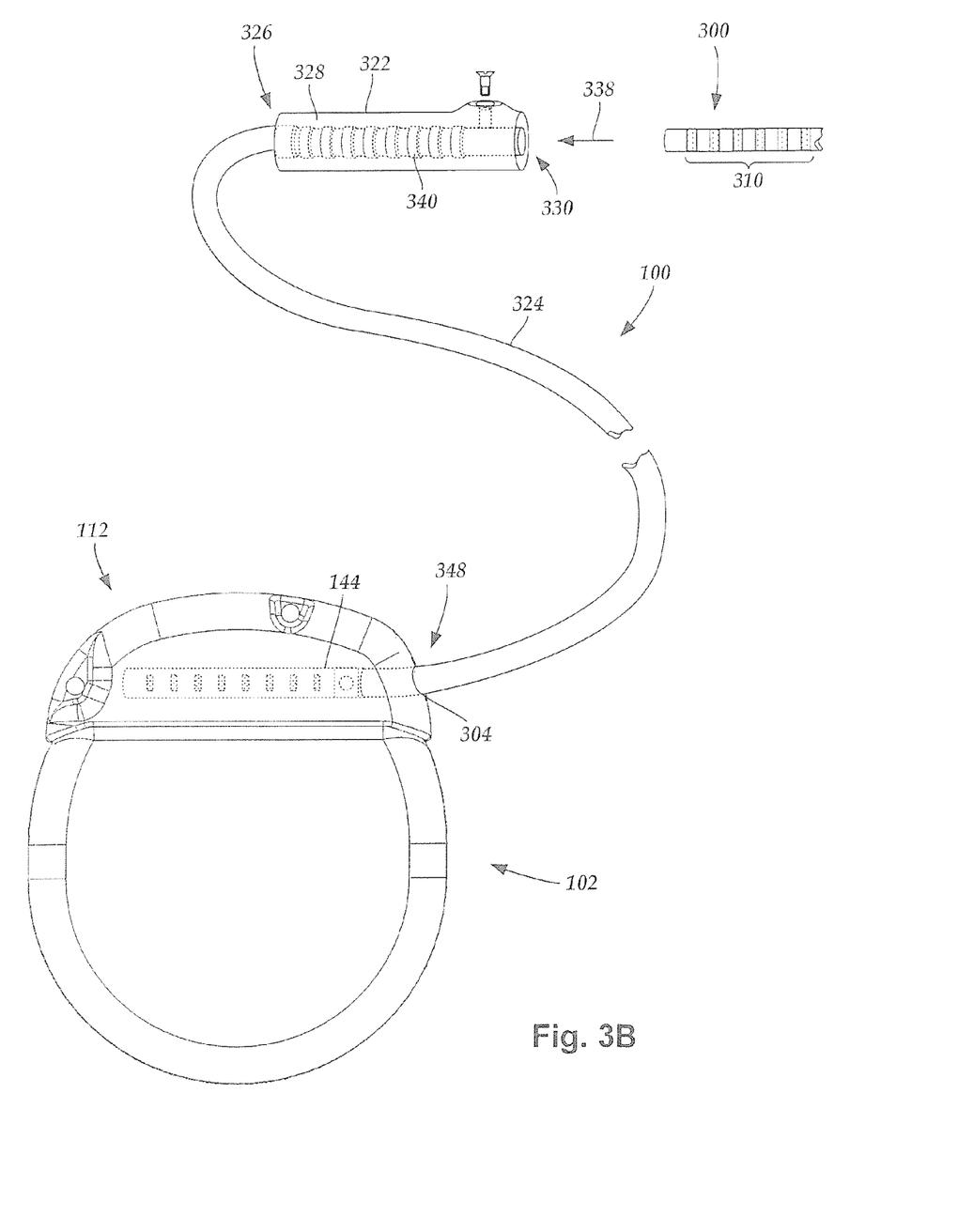
FIG. 3B is a schematic view of one embodiment of a lead extension configured and arranged to electrically couple the elongated device of FIG. 3A to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens is flushed continually, or on a regular basis, with saline, epidural fluid, or the like. In at least some embodiments, the one or more lumens can be permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 200, or both.

A lead extension connector 322 is disposed on the lead extension 374. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 are electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4A:
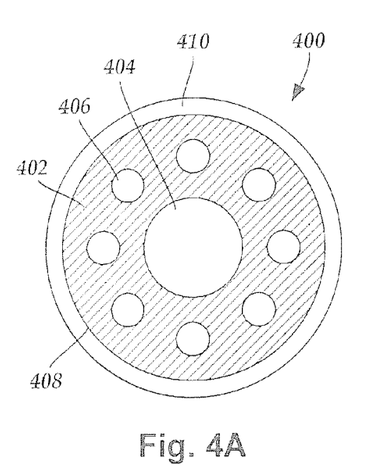
FIG. 4A is a schematic transverse cross-sectional view of one embodiment of the lead of FIG. 1 or FIG. 2, the lead including a multi-lumen conductor guide that defines a central lumen and a plurality of conductor lumens arranged around the central lumen, according to the invention.

Turning to FIG. 4A, in at least some embodiments, the lead includes a lead body with an elongated multi-lumen conductor guide having one or more conductor lumens (preferably, multiple conductor lumens) arranged about a central lumen. In at least some embodiments, the conductor lumens are arranged about the central lumen such that there are no other lumens extending along the multi-lumen conductor guide between the central lumen and each of the multiple conductor lumens. In some embodiments, the conductor lumens are each configured and arranged to receive a single conductor. In other embodiments, at least one of the conductor lumens is configured and arranged to receive multiple conductors.

FIG. 4A is a transverse cross-sectional view of one embodiment of the lead 400. The lead 400 includes an elongated multi-lumen conductor guide 402. The multi-lumen conductor guide 402 may extend an entire longitudinal length of the lead 400 from the electrodes 134 (FIG. 1 and FIG. 2) to the terminals 310 (FIGS. 3A and 3B). As shown in FIG. 4A, the multi-lumen conductor guide 402 defines a central lumen 404 and a plurality of conductor lumens, such as conductor lumen 406. The conductor lumens can have any suitable cross-sectional shape (e.g., round, oval, rectangular, triangular, or the like).

In at least some embodiments, the plurality of conductor lumens 406 are encapsulated by the multi-lumen conductor guide 402 such that the conductor lumens 406 do not extend to an outer surface 408 of the multi-lumen conductor guide 402. In which case, when conductors (420 in FIG. 4B) are disposed in the conductor lumens 406, the conductors are not exposed along the outer surface 408 of the multi-lumen conductor guide 402. The central lumen 404 and the plurality of conductor lumens 406 can be arranged in any suitable manner. In preferred embodiments, the conductor lumens 406 are disposed in the multi-lumen conductor guide 402 such that the conductor lumens 406 are peripheral to the central lumen 404. In at least some embodiments, the lead 400 may include one or more outer coatings of material 410 disposed over the outer surface 408 of multi-lumen conductor guide 402.

Figure 4B:
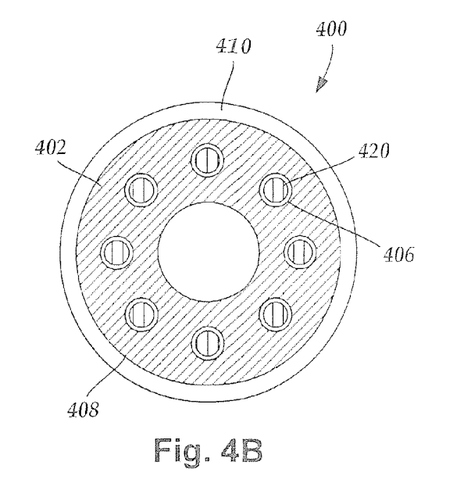
FIG. 4B is a schematic transverse cross-sectional view of one embodiment of conductors disposed in each of a plurality of conductor lumens of the multi-lumen conductor guide of FIG. 4A such that a different single conductor is disposed in each of the conductor lumens, according to the invention.

The plurality of conductor lumens 406 are configured and arranged to receive conductors, which electrically couple the electrodes 134 (FIG. 1 and FIG. 2) to the terminals 310 (FIGS. 3A) and 3B. FIG. 4B is a transverse cross-sectional view of one embodiment of conductors, such as conductor 420, disposed in the conductor lumens 406. In an embodiment, the conductor lumen 406 is of sub-millimeter diameter.

The multi-lumen conductor guide 402 can be formed of any suitable material including, but not limited to, polyurethane, silicone, or silicone-polyurethane copolymer. It will be recognized that the multi-lumen conductor guide need not have the specific form illustrated in FIGS. 4A and 4B and that other conductor guide arrangements can be used including arrangements that permit more than one conductor per lumen or includes fewer conductor lumens (in some instances, a single conductor lumen). In some embodiments, the conductor guide may be formed around the conductors by molding or other methods. In some embodiments, the conductor guide may be formed first and then the conductors inserted into the conductor guide.

Figure 5A:
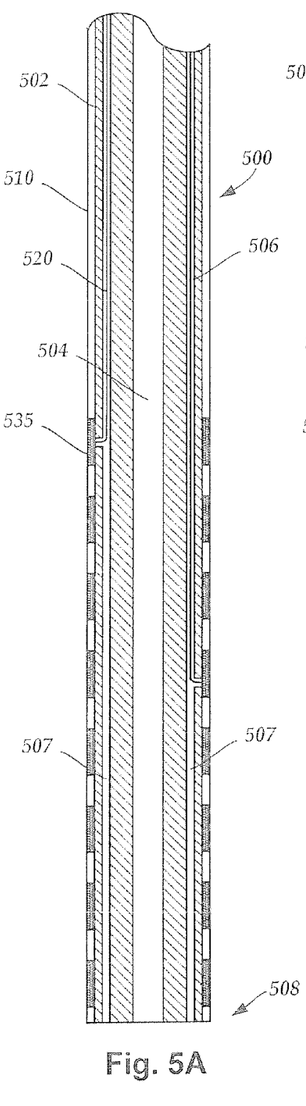
FIG. 5A is a schematic cross-sectional view of one embodiment of a proximal portion of a lead with unfilled or unstiffened conductor lumens, according to the invention.

FIG. 5A illustrates the proximal portion of a lead 500 with a lead body that includes a conductor guide 502. The conductor guide 502 includes a central lumen 504 surrounded by conductor lumens 506. Although the cross-sectional view of FIG. 5A depicts two conductor lumens 506, it will be understood that additional conductor lumens can be present and disposed circumferentially around the central lumen. The diameter of the lumens 506 may be the same or different. For example, one or more of the conductor lumens 506 may be narrower than the diameter of other conductor lumens 506. In at least one embodiment, the central lumen 504 and the conductor lumens 506 form hollow tubes that extend through the length of the conductor guide 502. The central lumen 504 and the conductor lumen 506 may extend from the proximal end 508 of the lead 500 to the distal end (not shown) of the lead 500. The conductor guide 502 is formed of a biocompatible, non-conductive material, for example, a polymeric material.

The outer surface of the conductor guide 502 may be coated with one or more outer layers 510. One or more terminals 535 are disposed on along the proximal portion of the lead 500. The terminals 535 can be separated by the outer layer 510 or any other suitable material that insulates the terminals 535 from each other. Such materials may include, for example, polymeric materials, such as silicone, polyurethane, or other thermoplastic materials. The terminals 535 are electrically attached to one or more conductors 520.

Each of the conductor lumens 506 inside the conductor guide 502 typically, but not necessarily, contains one or more of the conductors 520. The proximal end of each conductor 520 is coupled to one of the terminals 535 while the distal end of the conductor 520 is coupled to one or more of the electrodes 134 (FIG. 1). The terminals 535 are distributed in a longitudinally spaced apart arrangement.

The central lumen 504 may provide for stylet access and is empty when the stylet is not disposed in the lead. The stylet is typically used to facilitate implantation of the lead into the patient's body.

Figures 5B, 5C:
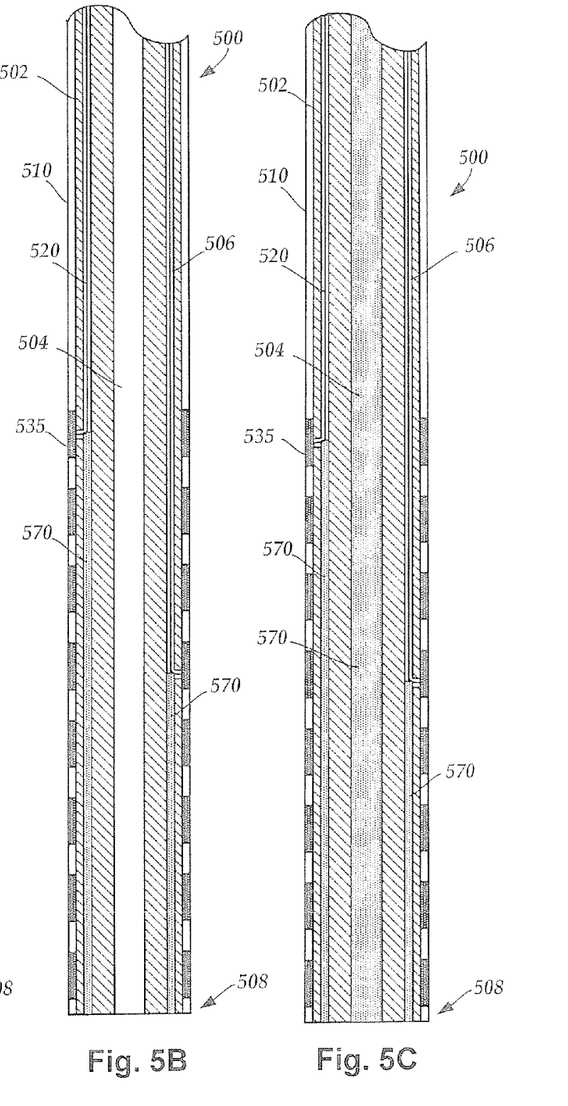
FIG. 5B is a schematic cross-sectional view of one embodiment of a proximal portion of a lead with portions of conductor lumens having monofilament stiffener material disposed therein, according to the invention.
FIG. 5C is a schematic cross-sectional view of one embodiment of a proximal portion of a lead with portions of conductor lumens and a central lumen having monofilament stiffener material disposed therein, according to the invention.

As illustrated in FIG. 5A, the proximal portion 507 of each conductor lumen 506 is empty from the proximal end 508 of the lead 500 to the point near which the conductor disposed within that conductor lumen couples to one of the terminals. A stiffening agent 570, for example, a monofilament material, can be disposed in the proximal portion of the conductor lumens 506 of the lead 500, as illustrated in FIG. 5B. This typically, but not necessarily, occurs during manufacture of the lead.

In at least some embodiments, the stiffening agent 570 is disposed in the conductor lumen 506 up to the point at which the conductor 520 resides, as illustrated in FIG. 5B. The stiffening agent 570 (e.g., the monofilament material) may be inserted into the void spaces in the conductor lumen 506 that are not filled by, or otherwise contain, the conductor 520. In other embodiments, the stiffening agent 570 may be inserted to a point proximal to the conductor 520 or to a point past the conductor 520. Preferably, the stiffening agent 570 is inserted into each of the conductor lumens 560, but in some embodiments, the stiffening agent 570 is inserted only some of the conductor lumens or only one of the conductor lumens, leaving one or more of the conductor lumens without stiffening agent.

The stiffening agent may be any suitable biocompatible material including polymeric materials such as, for example, silicone, polyurethane, or any other suitable material. In at least some embodiments, the stiffening agent is a polymeric material having a durometer or hardness which is at least 10%, 15%, or 25% greater than a durometer or hardness of the polymeric material of the conductor guide 502. Using of stiffening agent 570 of higher durometer than the material of conductor guide 502 can provide additional strength and stiffness to the proximal portion of the lead 500 and may protect it against mechanical stresses during clinical use. In at least some embodiments, the stiffening agent 570 is a monofilament material.

In at least some embodiments, the polymeric material of the stiffening agent 570 is melted or reflowed within the conductor lumen 506 after being placed therein. In at least some embodiments, the proximal portion of the lead 500 with the monofilament material of the stiffening agent 570 is heated to a temperature suitable for melting or reflowing the stiffening agent. The temperature that may he used, for example, for polyurethane material may be in the range of 140 to 250 degrees Celsius for a period of in the range of for example, 15 to 120 seconds. The temperature to which the conductor guide 502 is subjected may be just below, or just above, the melting temperature of the stiffening agent 570. At this temperature, the stiffening agent 570 may reflow and thermally fuse with the conductor guide 502 to create a continuous material.

FIG. 5C illustrates another embodiment in which the stiffening agent is disposed in both the conductor lumens 506 and the central lumen 504. The same or a different stiffening agent 570 may be disposed in the central lumen 504 and the conductor lumens 506. In some embodiments, the stiffening agent 570 in the central lumen 504 may extend to a point distal to all of the terminals, as illustrated in FIG. 5C, or to the most distal terminal or to any point between the most distal terminal and the proximal end 508 of the lead.

Figure 6A:
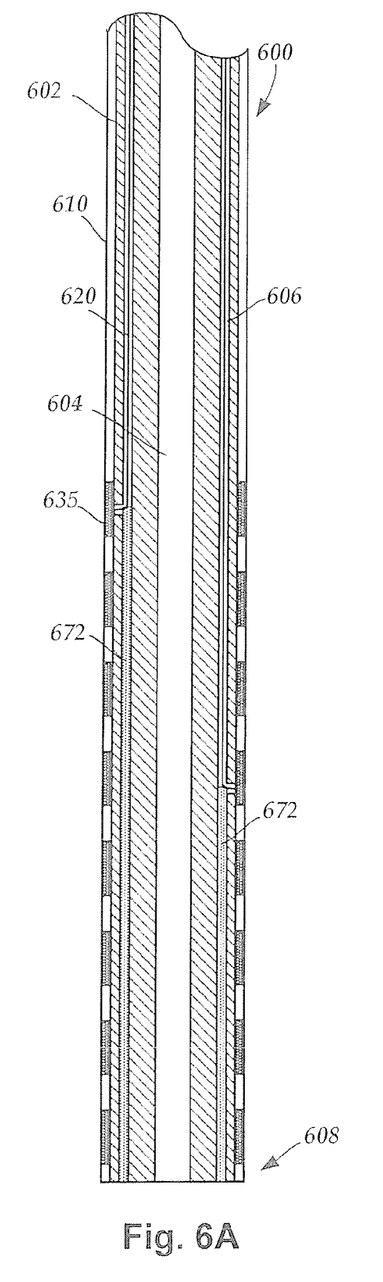
FIG. 6A is a schematic cross-sectional view of one embodiment of a proximal portion of a lead with portions of conductor lumens having epoxy disposed therein, according to the invention.

Instead of a monofilament material, the stiffening agent may be epoxy or an epoxy composite material. FIG. 6A illustrates the proximal portion of a lead 600 with conductor lumens 606 of a conductor guide 602 with epoxy 672 disposed in the conductor lumens. The conductor guide 602 defines a central lumen 604 with one or more surrounding conductor lumens 606. The lead 600 also includes a lead body with one or more outer layers 610 and an array of terminals 635.

The epoxy 672 can be introduced by flowing the material into the open portion of at least one of the conductor lumens 606. Thereafter, the epoxy 672 is cured. The curing process can be controlled through temperature, choice of resin and hardener compounds, or the ratio of the compounds, or the like.

In at least some embodiments, the epoxy 672 is disposed in the conductor lumen 606 up to the point at which the conductor 620 resides, as illustrated in FIG. 6A. The epoxy 672 may be inserted into the void spaces in the conductor lumen 606 that are not filled by, or otherwise contain, the conductor 620. In other embodiments, the epoxy 672 may be inserted to a point proximal to the conductor 620 or to a point past the conductor 620. Preferably, the epoxy 672 is inserted into each of the conductor lumens 660, but in some embodiments, the epoxy 672 is inserted only some of the conductor lumens or only one of the conductor lumens, leaving one or more of the conductor lumens without epoxy.

Figure 6B:
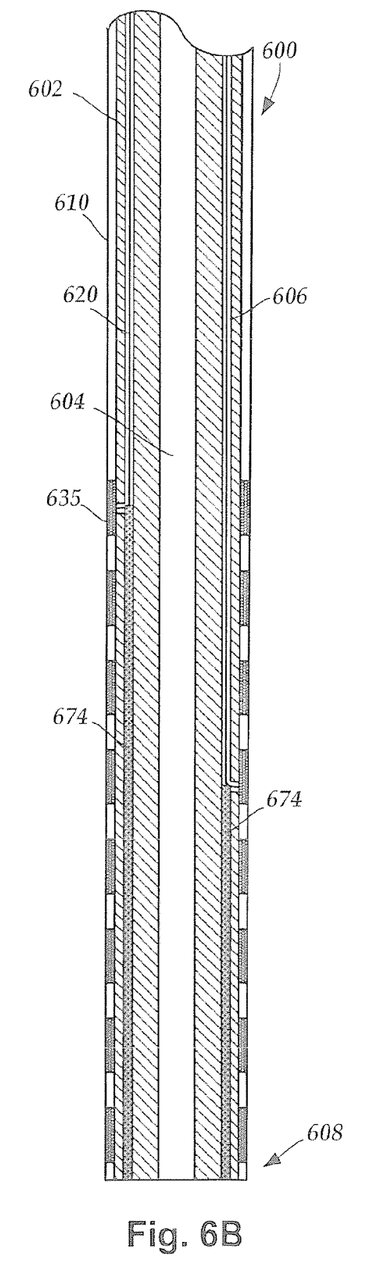
FIG. 6B is a schematic cross-sectional view of one embodiment of a proximal portion of a lead with portions of conductor lumens having epoxy broken into discrete particles disposed therein, according to the invention.

In at least some embodiments, the epoxy is then broken into discrete epoxy particles 674, as illustrated in FIG. 6B. Any suitable method can be used to break the epoxy into particles. For example, the cured epoxy can be broken by rolling the proximal end 608 of the lead 600 over a tool having a desired radius to break the cured epoxy material disposed within the conductor lumens 606 of the conductor guide 602 in a controlled manner. Alternately, the cured epoxy material may be broken by hand to form discrete epoxy particles 674.

Figure 6C:
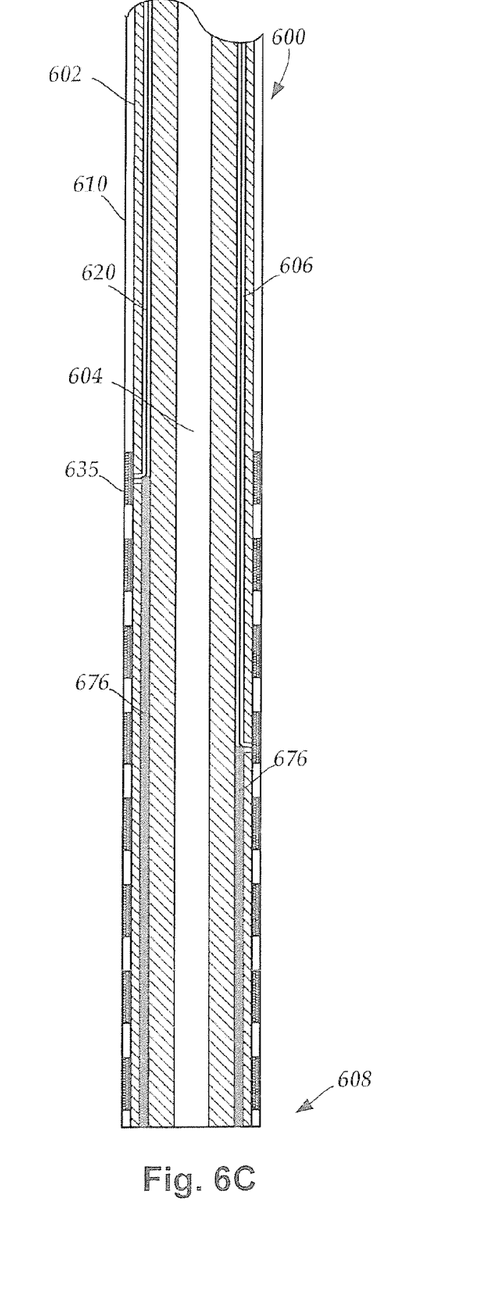
FIG. 6C is a schematic cross-sectional view of one embodiment of a proximal portion of a lead with portions of conductor lumens having a continuous epoxy layer surrounding discrete epoxy particles disposed therein, according to the invention.

In at least some embodiments, a second flowable epoxy material is introduced into at least one of (preferably, all of)

the conductor lumens 606 and around the discrete epoxy particles 674. This second flowable epoxy material is then cured to generate a cured second epoxy and form a continuous epoxy layer 676, as illustrated in FIG. 6C. The continuous epoxy layer 676 is a combination (e.g., an epoxy composite material) of discrete epoxy particles and the cured second epoxy.

Figure 6D:
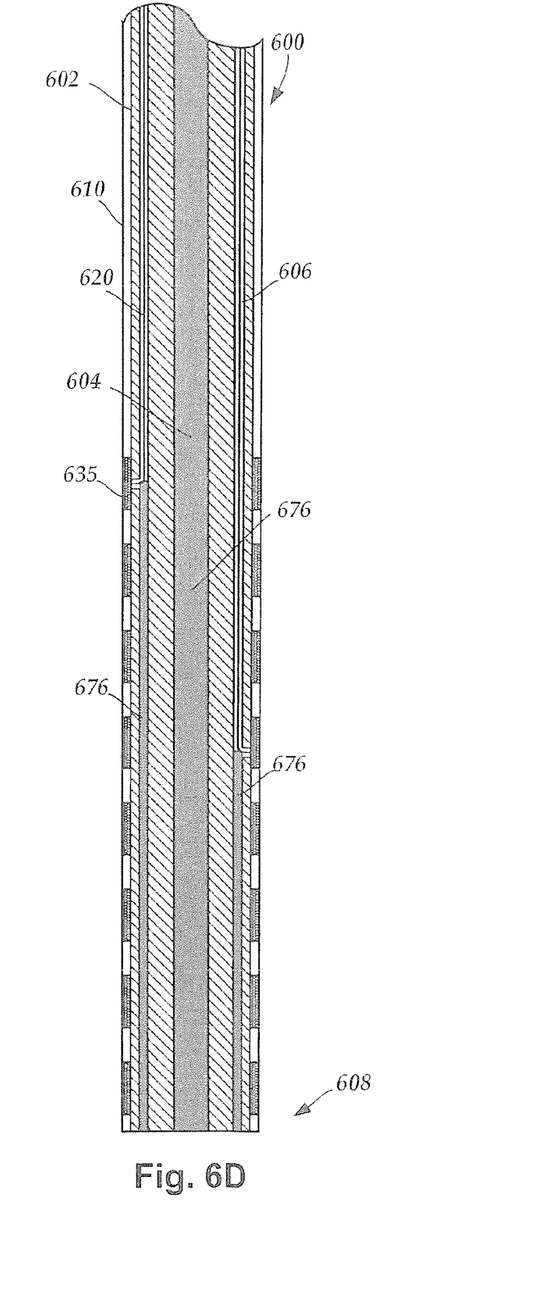
FIG. 6D is a schematic cross-sectional view of one embodiment of a proximal portion of a lead with portions of conductor lumens and a central lumen having a continuous epoxy layer surrounding discrete epoxy particles disposed therein, according to the invention.

FIG. 6D illustrates yet another embodiment with both the conductor lumens 606 and the central lumen 604 having the continuous epoxy layer 676. In some embodiments, the continuous epoxy layer 676 in the central lumen 604 may extend to a point distal to all of the terminals, as illustrated in FIG. 6D, or to the most distal terminal or to any point between the most distal terminal and the proximal end 608 of the lead.

Figure 7A:
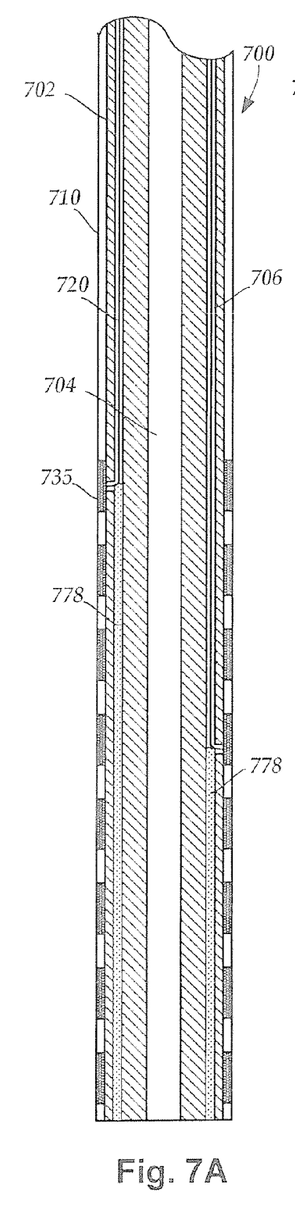
FIG. 7A is a schematic cross-sectional view of one embodiment of a proximal portion of a lead with portions of conductor lumens having a granular particulate disposed therein, according to the invention.

Instead of a monofilament material or epoxy, granular particulate material can be used as a stiffening agent. FIG. 7A illustrates a proximal portion of a lead 700 with a conductor guide 702 with conductor lumens 706 having a granular particulate 778 disposed therein. The conductor Guide 702 also defines a central lumen 704. One or more conductors 720 pass through the conductor lumens 706 and are electrically coupled to terminals 735 disposed along the proximal portion of the lead 700. The lead 700 also includes an outer layer 710.

The proximal portion of the conductor lumens 706 are filled with granular particulate 778. Any suitable granular particulate can be used, including, but not limited to ceramic or polymeric granular particulates or combinations thereof.

n at least some embodiments, the granular particulate 778 is disposed in the conductor lumen 706 up to the point at which the conductor 720 resides, as illustrated in FIG. 7A. The granular particulate 778 may be inserted into the void spaces in the conductor lumen 706 that are not filled by, or otherwise contain, the conductor 720. In other embodiments, the granular particulate 778 may be inserted to a point proximal to the conductor 720 or to a point past the conductor 720. Preferably, the granular particulate 778 is inserted into each of the conductor lumens 760, but in some embodiments, the granular particulate 778 is inserted only some of the conductor lumens or only one of the conductor lumens, leaving one or more of the conductor lumens without granular particulate.

In some embodiments, the granular particulate 778 and the conductor guide 702 may be heated thermally reflow or, alternatively to melt the granular particulate or the conductor guide or both. In some embodiments, a temperature is chosen such that one material melts while the other material thermally reflows. In at least some embodiments, the granular particulate melts and combines with the material of the conductor guide 702. In at least some embodiments, the granular particulate 778 is a reflowed granular particulate 780, as depicted in FIG. 7B.

Figures 7B, 7C:
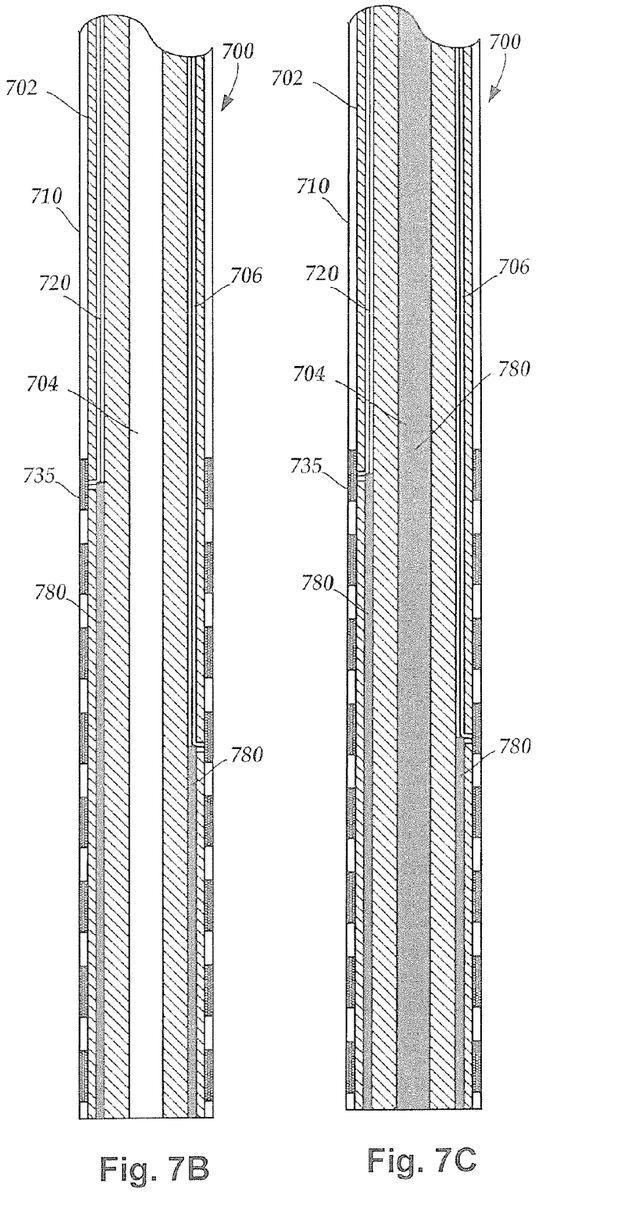
FIG. 7B is a schematic cross-sectional view of one embodiment of a proximal portion of a lead with portions of conductor lumens having a melted or reflowed granular particulate disposed therein, according to the invention.
FIG. 7C is a schematic cross-sectional view of one embodiment of a proximal portion of a lead with portions of conductor lumens and a central lumen having a melted or reflowed granular particulate disposed therein, according to the invention.

FIG. 7C illustrates yet another embodiment with both the conductor lumens 706 and the central lumen 704 having the reflowed granular particulate 780. In some embodiments, the reflowed granular particulate 780 in the central lumen 704 may extend to a point distal to all of the terminals, as illustrated in FIG. 7C, or to the most distal terminal or to any point between the most distal terminal and the proximal end of the lead.

Figure 8:
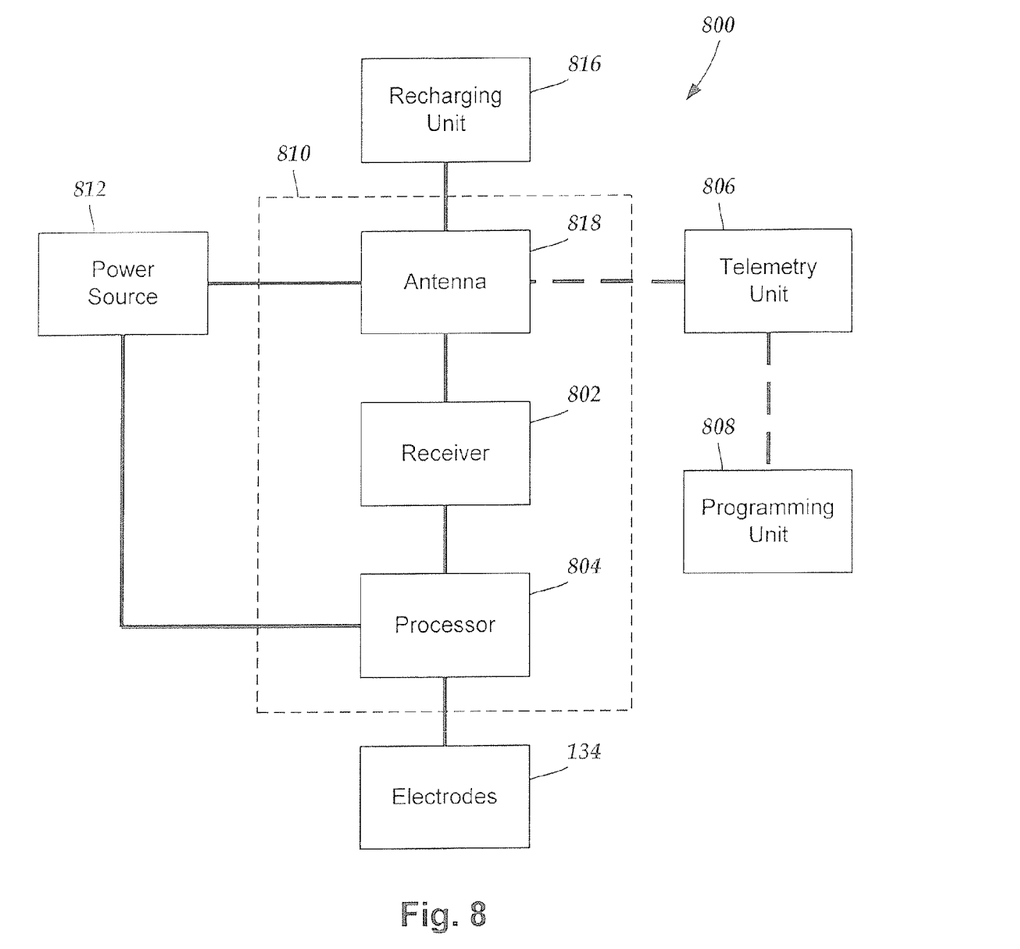
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment. the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead having a distal portion, the electrical stimulation lead comprising:
    a lead body having a distal portion, a proximal portion, and a longitudinal length;
    a plurality of electrodes disposed along the distal portion of the electrical stimulation lead;
    a plurality of terminals disposed along the proximal portion of the lead body;
    a plurality of conductors electrically coupling the plurality of terminals to the plurality of electrodes;
    a conductor guide disposed within the lead body and extending from the proximal portion of the lead body along the lead body, the conductor guide defining a central lumen and a plurality of conductor lumens disposed around the central lumen, the central lumen and conductor lumens extending longitudinally along the conductor guide, the conductor lumens having a proximal end and receiving the plurality of conductors within the conductor lumens; and
    a stiffening agent disposed within, and filling, at least one of the conductor lumens from the proximal end to at least a portion of the conductor lumen within which at least one of the conductors is disposed, wherein the stiffening agent comprises discrete epoxy particles and a continuous epoxy layer within which the epoxy particles are disposed.

2. The electrical stimulation lead of claim 1, wherein the stiffening agent is formed by flowing a flowable epoxy material around the epoxy particles and then curing the flowable epoxy material to generate the continuous epoxy layer.

3. The electrical stimulation lead of claim 1, wherein the stiffening agent is also disposed in a portion of the central lumen.

4. The electrical stimulation lead of claim 3, wherein the continuous epoxy layer of the stiffening agent disposed in the central lumen extends to a point distal of all of the terminals.

5. The electrical stimulation lead of claim 3, wherein the continuous epoxy layer of the stiffening agent disposed in the central lumen extends to a point between a distal-most one of the terminals and a proximal end of the central lumen.

6. The electrical stimulation lead of claim 1, wherein the plurality of electrodes is disposed along the distal portion of the lead body.

7. The electrical stimulation lead of claim 1, wherein the discrete epoxy particles are broken epoxy particles formed by breaking up an epoxy material.

8. The electrical stimulation lead of claim 1, wherein the stiffening agent is disposed within each of the conductor lumens.

9. The electrical stimulation lead of claim 1, wherein the stiffening agent is not disposed in at least one of the conductor lumens.

10. The electrical stimulation lead of claim 1, further comprising a paddle body coupled to the distal portion of the lead body, wherein the plurality of electrodes are disposed on the paddle body.

11. The electrical stimulation lead of claim 10, wherein the stiffening agent is formed by flowing a flowable epoxy material around the epoxy particles and then curing the flowable epoxy material to generate the continuous epoxy layer.

12. The electrical stimulation lead of claim 10, wherein the stiffening agent is also disposed in a portion of the central lumen.

13. The electrical stimulation lead of claim 12, wherein the continuous epoxy layer of the stiffening agent disposed in the central lumen extends to a point distal of all of the terminals.

14. The electrical stimulation lead of claim 12, wherein the continuous epoxy layer of the stiffening agent disposed in the central lumen extends to a point between a distal-most one of the terminals and a proximal end of the central lumen.

15. A method of making the electrical stimulation lead of claim 1, the method comprising:
    disposing a plurality of conductor wires into a plurality of conductor lumens defined within a conductor guide, the conductor lumens extending longitudinally from a proximal end of the conductor guide, wherein at least one of the conductor lumens defines an open portion that extends distally from the proximal end of the conductor guide and does not contain any portion of the conductors;
    disposing a plurality of terminals along the proximal portion of the conductor guide in a spaced-apart longitudinal arrangement;
    electrically coupling each of the plurality of terminals to at least one of the conductors;
    flowing epoxy material into the open portion of at least one of the conductor lumens;
    curing the epoxy material;
    breaking the cured epoxy material into discrete epoxy particles;

flowing additional epoxy material into the open portion of at least one of the conductor lumens and around the epoxy particles; and curing the additional epoxy material to form the continuous epoxy layer having the epoxy particles disposed therein.

16. The method of claim 15, wherein the conductor lumens are disposed circumferentially around the central lumen.

17. The method of claim 16, further comprising
flowing epoxy material into a proximal portion of the central lumen, and
curing the epoxy material in the proximal portion of the central lumen.

18. The method of claim 17, further comprising
breaking the cured epoxy material in the central lumen into discrete epoxy particles.

19. The method of claim 18, further comprising
flowing additional epoxy material into the proximal portion of the central lumen and around the epoxy particles; and
curing the additional epoxy material to form a continuous epoxy layer having the epoxy particles disposed therein.

20. The method of claim 15, wherein breaking the cured epoxy material comprises rolling the conductor guide over a tool having a desired radius to break the cured epoxy material disposed within the conductor lumens of the conductor guide.

* * * * *